(12) United States Patent
Coggins

(10) Patent No.: US 7,860,546 B2
(45) Date of Patent: Dec. 28, 2010

(54) MEDICAL ELECTRODE WITH SELF-LIFTING TABS

(75) Inventor: Scott R. Coggins, Palmer, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 977 days.

(21) Appl. No.: 11/444,926

(22) Filed: Jun. 1, 2006

(65) Prior Publication Data

US 2007/0282408 A1  Dec. 6, 2007

(51) Int. Cl.
*A61B 5/04* (2006.01)
(52) U.S. Cl. .................. 600/391; 600/385; 600/392
(58) Field of Classification Search .............. 600/391, 600/392
See application file for complete search history.

(56) References Cited

U.S. PATENT DOCUMENTS

| | | | | |
|---|---|---|---|---|
| 3,998,215 A | * | 12/1976 | Anderson et al. | 600/397 |
| 4,543,958 A | * | 10/1985 | Cartmell | 600/391 |
| 4,640,289 A | * | 2/1987 | Craighead | 600/391 |
| 4,643,193 A | * | 2/1987 | DeMarzo | 600/392 |
| 4,674,511 A | * | 6/1987 | Cartmell | 600/385 |
| 4,694,835 A | * | 9/1987 | Strand | 600/385 |
| 4,922,911 A | * | 5/1990 | Wada et al. | 600/391 |
| 5,337,748 A | | 8/1994 | McAdams et al. | |
| 6,745,082 B2 | * | 6/2004 | Axelgaard | 607/142 |

* cited by examiner

*Primary Examiner*—Lee S Cohen
(74) *Attorney, Agent, or Firm*—Lisa E. Winsor, Esq.

(57) ABSTRACT

A medical electrode includes a backing layer having a top face and a bottom face, and a shrinkable layer covering at least a portion of the top face of the backing layer. Shrinkage of the shrinkable layer results in flexing of a portion of the backing layer to aid placement and attachment of the electrode to the patient.

28 Claims, 5 Drawing Sheets

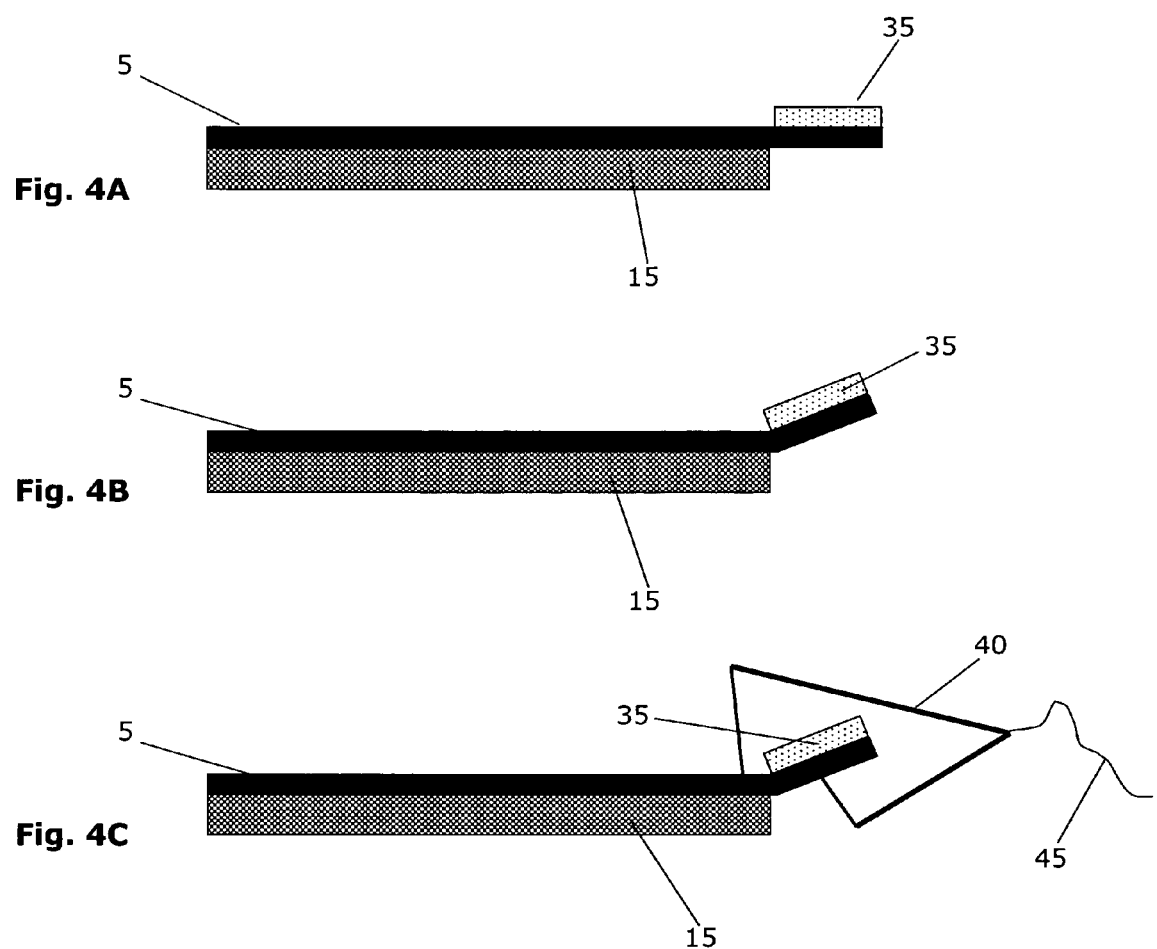

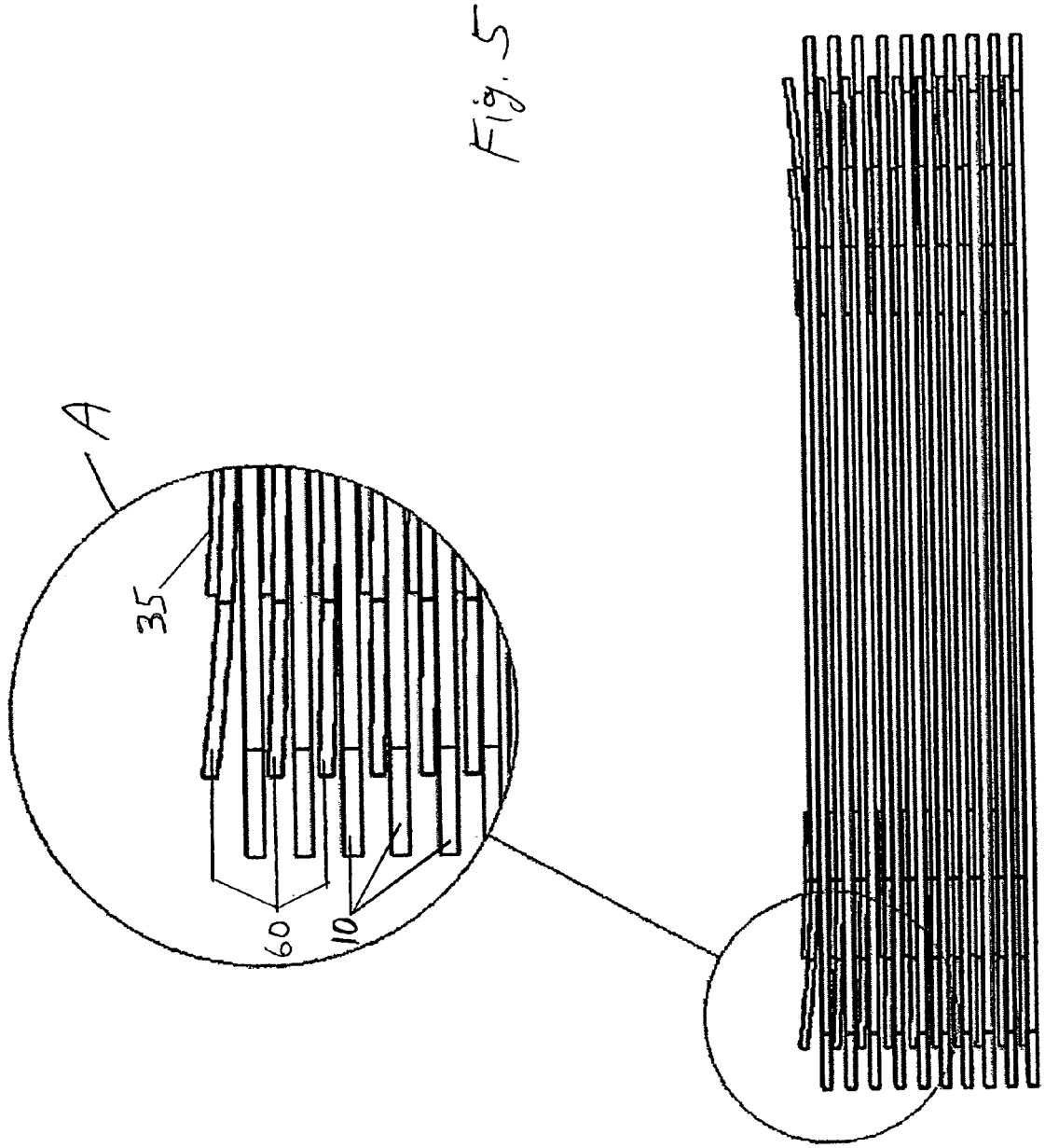

MEDICAL ELECTRODE WITH SELF-LIFTING TABS

FIELD OF THE INVENTION

The invention is in the field of medical electrodes, and more particularly to disposable medical electrodes.

BACKGROUND OF THE INVENTION

Biomedical electrodes useful for patient diagnostic and monitoring applications are well known in the art. In the use of medical electrodes, such as those used to obtain an electrocardiogram trace (ECG), a practitioner attaches one or more electrodes to the patient's body and connects the electrodes to an electrical, diagnostic, therapeutic, or electrosurgical equipment. Biomedical electrodes comprise a conductive medium contacting the patient's skin and a means for electrical communication between the conductive medium and the electrical equipment. Biomedical tab electrodes generally comprise an electrically conductive tab, extension, or other protrusion extending from the periphery of the electrode that is attached to the equipment by means of alligator clips or other conductive attachment device. Connecting multiple electrodes to a patient for diagnostic and monitoring applications is a time consuming and repetitive task for the practitioner, requiring a certain degree of dexterity and care in order to make proper use of the electrode and prevent damage or contamination.

SUMMARY OF THE INVENTION

These actions can be made easier for the practitioner if the electrode has a tab or other protrusion which, in an unstressed configuration, automatically flexes toward the practitioner and away from the patient's skin. Such a design is desirable to aid the practitioner in quick and efficient placement of the electrodes. Further, such a design is desirable to aid the practitioner in attaching clips to the electrode.

A shrinkable layer is attached to a portion of a backing layer on one side of a medical electrode. Shrinkage of the shrinkable layer causes a portion of the backing layer to flex, or bend, in a direction toward the shrinkable layer.

BRIEF DESCRIPTION OF THE FIGURES

FIGS. 4A, 4B, and 4C show cross-sections of another embodiment of an electrode with a self-lifting tab.

FIG. 5 shows a stack of electrode cards with the tabs lifted on the uppermost cards.

DETAILED DESCRIPTION OF THE INVENTION

Figure 1A:
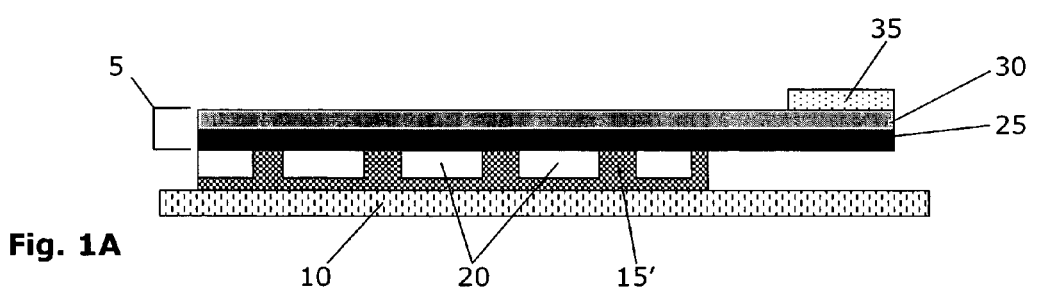
FIGS. 1A, 1B, and 1C show cross sections of one embodiment of an electrode with a self-lifting tab and a composite backing layer.

FIGS. 1-5 illustrate embodiments of a medical electrode with a self-lifting tab. The embodiments and FIGS. 1-5 are to be interpreted as exemplary, not limiting. In accordance with common practice, the figures are not drawn to scale, and corresponding features in FIGS. 1-5 are indicated by the same guide numbers.

FIGS. 4A, B, and C show a cross section of a first embodiment of an electrode with self-lifting tab. Electrically conductive layer 15 and flexible backing layer 5 form a basic electrode structure. Backing layer 5 may be an electrically non-conductive film. It may also be opaque to visible, infra-red and ultra-violet light, which will reduce light-induced electrical noise. A shrinkable layer 35 is applied to a portion of the backing layer 5 that is not in contact with the conductive layer 15. Shrinkable layer 35 is applied to the top of top face of backing layer 5 during fabrication of the electrode. Shrinkable layer 35 may be in the form of a single contiguous region, as shown in FIGS. 4A-C, or in the form of a plurality of non-contiguous regions, such as a pattern of disconnected circles. To allow the obtaining of x-ray images of the patient with the electrodes in place, the layers 5, 15, and 35 may be made translucent to x-rays.

Once applied, layer 35 may also begin to decrease in volume, or shrink, with or without additional treatment. With layer 35 strongly adhered to flexible backing layer 5, shrinkage of layer 35 causes backing layer 5 to flex, or bend, in a direction toward shrinkable layer 35 and away from conductive layer 15. The flexing is shown in FIG. 4B. The flexing is driven by stress on backing layer 5 arising from the shrinking of shrinkable layer 35. The flexing makes it easier for a medical practitioner to remove the electrode from a package, attach it to a patient, and electrically attach it to a monitoring device (not shown).

Shrinking of shrinkable layer 35 may be brought about by exposure of the layer to light, heat, charged particles, or other forms of energy in any combination. Shrinkage may occur due to the evaporation of a solvent from shrinkable layer 35.

Shrinkable layer 35 may be applied as a liquid, such as a varnish or a polymer solution. A specific example is the ultraviolet-curable varnish designated RC1188 available from Sun Chemical (Parsippany, N.J.) and EICEC027 available from Environmental Inks & Coatings (Morganton, N.C.). Also usable as shrinkable layers are varnishes or other materials which are cured by exposure to an electron beam. Still another category of suitable materials for shrinkable layer 35 is room-temperature vulcanizing (RTV) materials. The amount of bending of base layer 5 may be controlled by varying the thickness (coat weight) of the shrinkable layer 35 and varying the degree of crosslinking in shrinkable layer 35. Another way to control the amount of bending for a given shrinkable material may be to vary the amount of material dissolved in a solvent—a more dilute varnish or polymer solution may result in a lesser degree of bending.

Other examples of shrinkable layer materials useful for shrinkable layer 35 are solid films which may be bonded to backing layer 5 and then treated to induce shrinkage, by heating, for example. The solid film could be a polymer film, containing, for example, polyolefins such as linear, low density polyethylene or polypropylene. For heat shrinking, many polyolefin films have this property.

Shrinkable layer 35 could also be deposited from the gas phase using, for example, chemical vapor deposition (CVD). If the deposition is done at elevated temperature, for example, the deposited film may shrink upon returning to room temperature. Metal films may be deposited in this manner. Suitable metals include aluminum, silver, and gold.

The upward flexing of a portion of the backing layer shown in FIG. 4B facilitates the preparation of the electrode, attachment of the electrode to the patient's skin, and attachment of electrical conductors to the electrode. FIG. 4C shows how an electrical conductor 45, such as a wire, might be electrically connected to the electrode by means of clip 40 once backing layer 5 has flexed. Conductor 45 may be connected at its other end to a medical instrument, such as an electrocardiograph or a defibrillator (not shown). Clip 40 may be of the "alligator" type, with a spring to hold the clip in good physical and electrical contact with the electrode. In the embodiment of FIG. 4C, the backing layer 5 is electrically conductive. Clip 40 makes electrical contact with backing layer 5. An electrically conducting path is thereby established from conductor 45 through, in succession, clip 40, backing layer 5, electrically conductive layer 15, and the patient (not shown). Electrical energy may flow in either direction along this path.

Electrically conductive layer 15 may be a conductive gel, such as a skin-compatible hydrogel. One such hydrogel is marketed by Tyco Healthcare Kendall-LTP division, Chicopee, Mass., under the trademark QTrace 5400. When the electrode is attached to a patient, the gel is in contact with the patient's skin and acts to establish a conducting path for conveying electrical energy between the patient's body and an apparatus, in either direction. A gel layer also serves to adhere the electrode to the patient's skin.

Figure 1B:
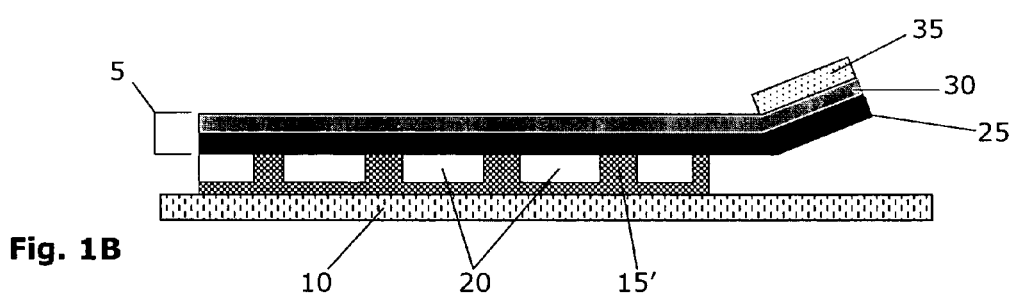
Figure 1C:
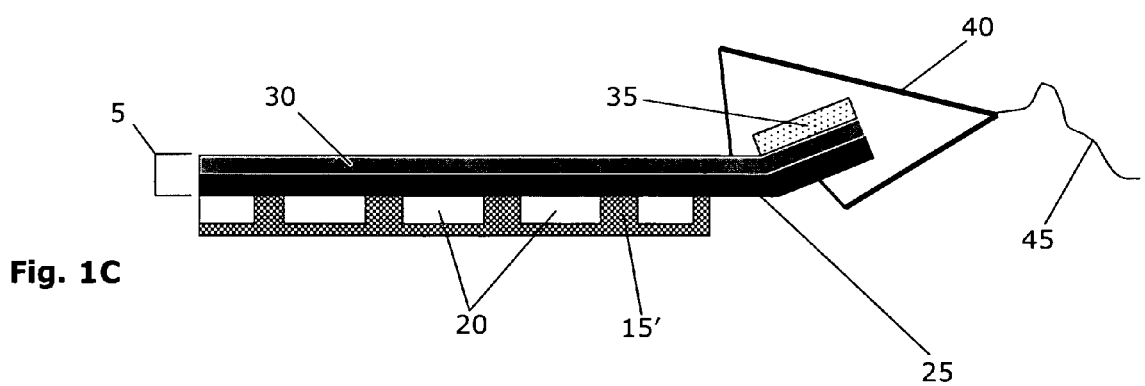

FIGS. 1A, 1B, and 1C show a cross-section of a second embodiment of an electrode with a self lifting tab. In this embodiment backing layer 5 contains two sublayers, 25 and 30, bonded together. Alternatively, additional sublayers may also be used. In particular, sublayer 25 may be electrically conductive while sublayer 30 may be electrically insulating. Either or both sublayers may be made opaque to visible, infra-red, and ultraviolet light. Suitable materials for an insulating sublayer 30 include non-conducting plastics. Suitable materials for conductive sublayer 25 include conductive polymers, such as carbon filled or metal filled polymers.

As in the first embodiment, a shrinkable layer 35 is applied to the top of backing layer 5, in contact with the topmost sublayer 30. As before, shrinking of shrinkable layer 35 causes the multilayer backing layer 5 to flex, as shown in FIGS. 1B and 1C.

Still referring to the embodiment of FIGS. 1A, B, C, below conducting sublayer 25, and in contact with it, is a discontinuous pattern 20 of a second electrically conductive material. This material may be a metal/metal chloride coating or ink, such as silver/silver chloride or tin/tin chloride. A metal/metal chloride coating may be applied by silk-screening or by flexographic printing.

An electrically conductive gel layer 15' covers and makes contact with both discontinuous pattern 20 and conducting sublayer layer 25. Discontinuous pattern 20 and gel layer 15' together form a composite electrically conductive layer which provides a conductive path between conductive layer 25 and the patient. In this embodiment, a release layer 10 covers the entire area of gel layer 15 prior to use of the electrode and protects gel layer 15' from contamination. Release layer 10 extends beyond the gel layer 15' on all sides. Suitable materials for release layer 10 include paper or a siliconized polymer such as silicone-coated polyethylene terephthalate (PET). When backing layer 5 flexes, due to the action of shrinkable layer 35, the separation between the backing layer 5 and the release layer 10 over the region of flexing is increased, as shown in FIG. 1B, facilitating the removal of the release layer by a practitioner.

FIG. 1C shows the second embodiment of the electrode after the release layer 10 has been removed. FIG. 1C also shows an electrical clip 40 and conductor 45 attached to the electrode. In this embodiment one side of the clip makes electrical contact with conducting sublayer 25. An electrically conducting path is then established through conductor 45, clip 40, conductive sublayer 25, discontinuous conductive pattern 20 and gel layer 15', to the patient. Electrical energy may also be conducted along the same path in reverse order.

Figure 2A:
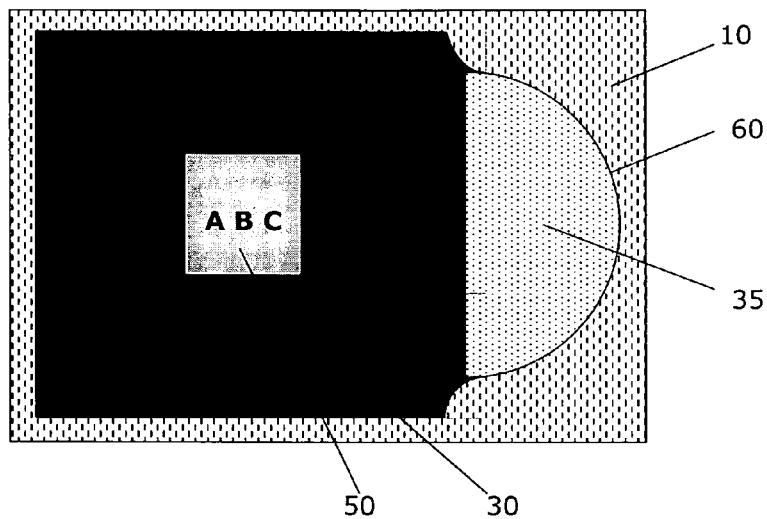
FIGS. 2A and 2B show plan views of two sides of an embodiment of an electrode with a self-lifting tab.
Figure 2B:
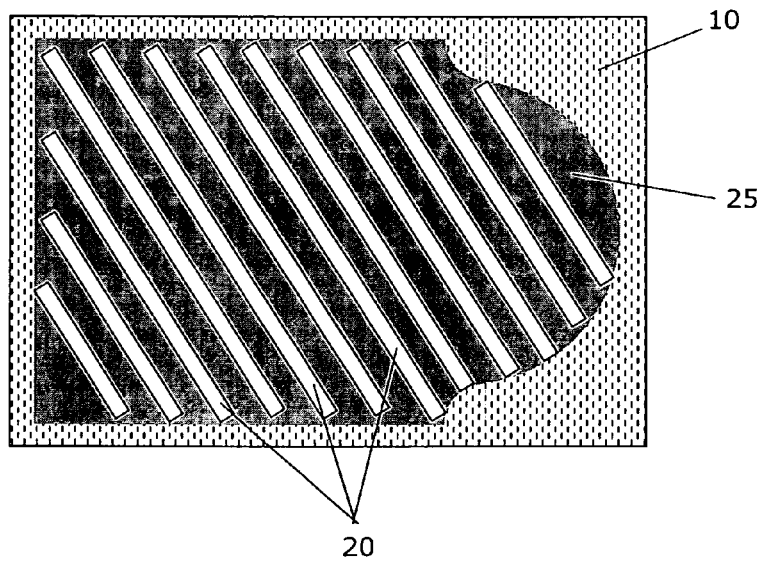

FIGS. 2A and 2B are respectively top and bottom plan views of an embodiment of the electrode similar to that shown in FIGS. 1A, 1B, and 1C, with corresponding reference numbers. Referring to FIG. 2A, a label 50 may be printed on the top face of top film 30 showing, for example, the logo of the electrode manufacturer. Shrinkable layer 35 is applied to protruding tab 60 shown here as having an essentially semi-circular shape. In this embodiment shrinkable layer 35 is shown applied essentially over the entire area of tab 60, but complete coverage of the tab area is not necessary to achieve sufficient flexing and lifting of the tab 60. In this embodiment the discontinuous conductive pattern 20 has the form of diagonal stripes, sometimes called "racing stripes".

Figure 3A:
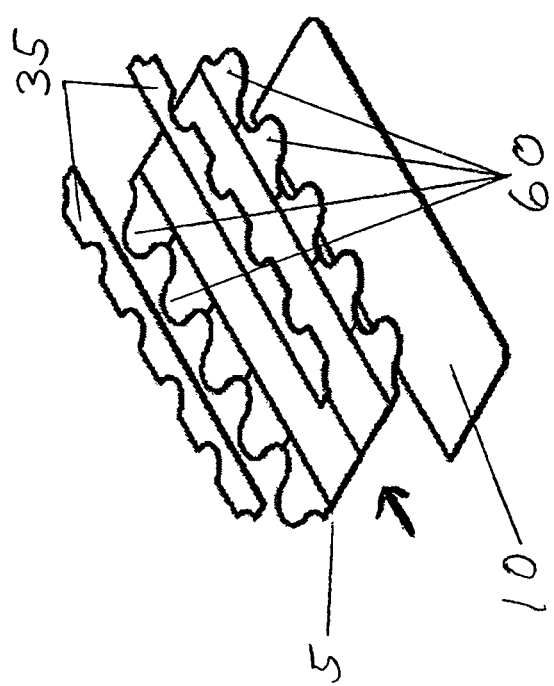
FIGS. 3A and 3B show a card containing multiple electrodes all having lifted tabs.
Figure 3B:
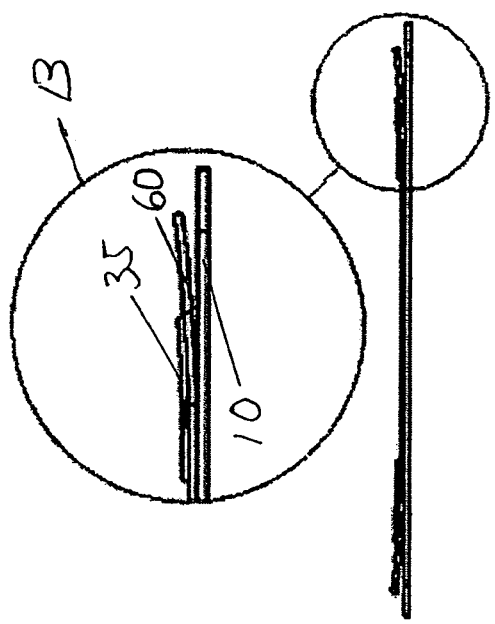

FIG. 3A is an exploded perspective view of a set of ten electrodes, with self lifting tabs, each of the type disclosed. The electrodes are all attached to one release layer 10, as they might be in an electrode set designed for acquiring an ECG trace. FIG. 3B is a side view of the card in FIG. 3A from the direction indicated by the arrow. As shown in the magnified portion B, each tab 60 of each electrode is in a lifted position, brought about by the shrinkage of shrinkable layer 35.

Electrode cards similar to that shown in FIG. 3 are often sold stacked together in a package. An example of such a stack is shown in FIG. 5. As shown in the magnified portion A, tabs 60 on a card may be held flat or partially flexed by the presence of the cards surrounding it in the stack. Tabs 60 of each electrode on the card at an end (top) of the stack will, however, be maximally flexed through the action of shrinkage of shrinkable layer 35, thereby facilitating the medical practitioner's job of peeling each electrode from release layer 10, attaching each electrode to the patient's body, and attaching conductor 45 to each electrode. Likewise, tabs 60 will fully lift on any card removed from anywhere in the stack.

In an alternate embodiment release layer 10 could be omitted. In one example of this embodiment, a plurality of electrodes could be attached to one another by linear perforated regions and wound into a roll, resembling a rolled sheet of postage stamps. While the electrodes are attached to one another each tab 60 remains coplanar with the remainder of the electrode, held there by the perforated attachments and the surrounding electrodes. The tab will flex when a practitioner separates an electrode from the roll by tearing at the perforations.

Shrinkable layer 35 may be applied to existing medical electrodes to create self-lifting tabs on these electrodes. An example of such electrodes is disclosed in FIGS. 1 and 1A of U.S. Pat. No. 5,337,748.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A medical electrode comprising:
   an electrically conductive layer;
   a backing layer having a top face and a bottom face, wherein at least a portion of the bottom face is in contact with the electrically conductive layer; and
   a shrinkable layer in contact with a portion of the top face of the backing layer, the shrinkable layer being (i) solely positioned on at least a portion of a perimeter of the backing layer, and (ii) defining a tab protruding outside a periphery of the conductive layer.

2. The electrode of claim 1, wherein the shrinkable layer has the form of a single contiguous region or a plurality of non-contiguous regions.

3. The electrode of claim 1, wherein the shrinkable layer comprises a material which shrinks when exposed to one or more of: light, heat, or charged particles.

4. The electrode of claim 3, wherein the shrinkable layer comprises a material which shrinks when exposed to ultra-violet light.

5. The electrode of claim 3, wherein the shrinkable layer comprises a material which shrinks when exposed to an electron beam.

6. The electrode of claim 1, wherein the shrinkable layer comprises a room-temperature vulcanizing material.

7. The electrode of claim 1, wherein the shrinkable layer comprises a varnish.

8. The electrode of claim 1, wherein the shrinkable layer comprises a solid film bonded to the backing layer.

9. The electrode of claim 8, wherein the solid film is a polymer film.

10. The electrode of claim 8, wherein the solid film is a metal film.

11. The electrode of claim 10, where the metal film is deposited using chemical vapor disposition.

12. The electrode of claim 1, wherein the backing layer comprises at least two sublayers, including a top sublayer containing the top face and a bottom sublayer containing the bottom face.

13. The electrode of claim 12, wherein at least one sublayer is electrically conductive.

14. The electrode of claim 12, wherein at least one sublayer is electrically non-conducting.

15. The electrode of claim 1, wherein the backing layer is opaque to infrared, visible, and ultra-violet light.

16. The electrode of claim 1, wherein the electrically conductive layer comprises an electrically conductive gel layer.

17. The electrode of claim 16 further comprising a discontinuous pattern of electrically conducting material contacting the bottom face of the backing layer, the electrically conductive gel layer covering the discontinuous pattern and contacting the bottom face of the backing layer.

18. The electrode of claim 1, wherein the electrically conducting layer, the backing layer, and the shrinkable layer are translucent to x-rays.

19. A medical electrode with a self-lifting tab, comprising:
an electrically conductive layer comprising a hydrogel, a discontinuous pattern of silver/silver chloride stripes in contact with the hydrogel and arrayed along diagonals with respect to the edges of the electrode,
a backing layer comprising at least one electrically non-conductive sublayer and at least one electrically conductive sublayer comprising a carbon film, the electrically conductive sublayer being in contact with the hydrogel and the non-conductive sublayer being in contact with the conducting sublayer, and
a UV-curable varnish layer in contact with a portion of the electrically non-conductive sublayer, the varnish layer being (i) solely positioned on at least a portion of a perimeter of the backing layer, and (ii) defining a tab protruding outside a periphery of the conductive layer.

20. A medical electrode comprising:
an electrically conductive layer;
a backing layer overlying the conductive layer, wherein a portion of the backing layer extends beyond a perimeter of the conductive layer to define a tab; and
a shrinkable layer solely overlying the tab.

21. The electrode of claim 20, wherein the tab protrudes entirely outside a periphery of the conductive layer.

22. The electrode of claim 20, wherein the shrinkable layer has the form of at least one of a single contiguous region and a plurality of non-contiguous regions.

23. The electrode of claim 20, wherein the shrinkable layer comprises a material which shrinks when exposed to at least one of light, heat, ultraviolet light, charged particles and an electron beam.

24. The electrode of claim 20, wherein the shrinkable layer comprises at least one of a room-temperature vulcanizing material and a varnish.

25. The electrode of claim 20, wherein the shrinkable layer comprises a solid film bonded to the backing layer.

26. The electrode of claim 25, wherein the solid film is one of a polymer film and a metal film.

27. The electrode of claim 20, wherein the electrically conductive layer comprises an electrically conductive gel layer.

28. The electrode of claim 20, wherein the electrically conductive layer, the backing layer, and the shrinkable layer are translucent to x-rays.

* * * * *